United States Patent [19]

Calvet et al.

[11] Patent Number: 5,472,970
[45] Date of Patent: Dec. 5, 1995

[54] ALLYLAMINOESTERS AND THEIR APPLICATION IN THERAPEUTICS

[75] Inventors: Alain P. Calvet, L'Hay-Les-Roses; Agnes G. Grouhel, Meudon; Jean-Louis Junien, Sevres, all of France

[73] Assignee: Institut De Recherche Jouveinal S.A., Fresnes Cedex, France

[21] Appl. No.: 309,004

[22] Filed: Sep. 19, 1994

Related U.S. Application Data

[63] Continuation-in-part of Ser. No. 58,698, May 3, 1993, Pat. No. 5,348,980.

[30] Foreign Application Priority Data

May 5, 1992 [FR] France ............... 92 05519
Oct. 15, 1993 [FR] France ............... 93 12301

[51] Int. Cl.$^6$ .................... A61K 31/22; A61K 31/235; A61K 31/44; C07D 213/55
[52] U.S. Cl. .................... 514/356; 514/354; 514/509; 514/530; 514/532; 514/546; 546/322; 546/326; 560/1; 560/58; 560/59; 560/73; 560/101; 560/102; 560/104; 560/105; 560/106; 560/122; 560/250
[58] Field of Search .................... 546/322, 326; 560/1, 58, 59, 73, 101, 102, 104, 105, 106, 122, 250; 514/354, 356, 529, 530, 532, 546

[56] References Cited

U.S. PATENT DOCUMENTS

| | | | |
|---|---|---|---|
| 4,994,617 | 2/1991 | Aubard et al. | 564/355 |
| 5,245,080 | 9/1993 | Aubard et al. | 564/346 |
| 5,266,599 | 11/1993 | Aubard et al. | 514/651 |
| 5,348,980 | 9/1994 | Aubard et al. | 514/653 |
| 5,362,756 | 11/1994 | Riviere et al. | 514/651 |
| 5,389,686 | 2/1995 | Diop et al. | 514/651 |

FOREIGN PATENT DOCUMENTS

| | | |
|---|---|---|
| 2378746 | 6/1983 | France . |
| 2690917 | 11/1993 | France . |
| 1434826 | 5/1976 | United Kingdom . |

OTHER PUBLICATIONS

Spickett et al., Chemical Abstracts, vol. 85 (1976) 14285h.
Aubard et al., Chemical Abstracts, vol. 120 (1994) 269849j.
U. Schollkpf, *Synthesis*, p. 969 (1981).

*Primary Examiner*—Richard L. Raymond
*Attorney, Agent, or Firm*—Pennie & Edmonds

[57] ABSTRACT

Allylaminoesters of the formula (I):

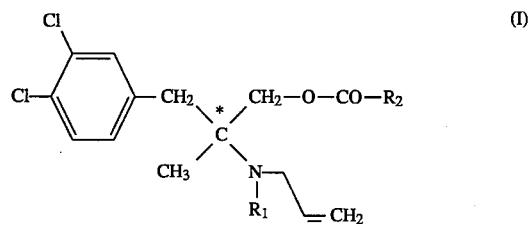

in which:

$R_1$ is H or low-molecular-weight alkyl, $R_2$ is low-molecular-weight alkyl, cycloalkyl, or low-molecular-weight phenylcycloalkyl, pyridyl or phenyl, low-molecular-weight phenylalkyl, low-molecular-weight diphenylalkyl, low-molecular-weight phenylalkenyl, in which the phenyl cycle may be mono-, di- or trisubstituted by chlorine atoms, low-molecular-weight alkyl radicals, low-molecular-weight alkoxy, or trifluoromethyl, acetamide or acetyloxy radicals, their racemic forms, their (S) enantiomers and their addition salts. Also, antiallergic drugs containing the same.

5 Claims, No Drawings

ALLYLAMINOESTERS AND THEIR APPLICATION IN THERAPEUTICS

This application is a continuation-in-part of application Ser. No. 08/058,698, filed May 3, 1993, now U.S. Pat. No. 5,348,980.

TECHNICAL FIELD

The present invention concerns esters derived from 2-allylamino-2(3,4-dichlorobenzyl)-n-propanol, their method of preparation and their applications, especially in therapeutics.

TECHNOLOGICAL BACKGROUND OF THE INVENTION

British Patent No. 1,434,826 describes esters and carbamates of amino alcohols having the general formula:

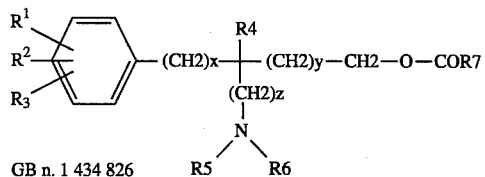

GB n. 1 434 826 in which $R_1$, $R_2$ and $R_3$ are hydrogen, alkyl, hydroxyalkyl, trifluoromethyl or halogen, $R_4$ is hydrogen, alkyl, cycloalkyl or aryl, $R_5$ and $R_6$ are hydrogen, alkyl, or aryl alkyl or together form a heterocyclic structure, and x, y and z are zero or one, $R_7$ being alkyl, aryl alkyl, aryl, aryl alkenyl, diaryl alkyl, aryl cycloalkylalkyl, heteroaryl, amino or amino-substituted.

These compounds are reported to be inhibitors of gastrointestinal spasms and peristalsis; some of them have analgesic properties, combined with a remarkable absence of activity with regard to the central nervous system.

In the French patent application published under No. 2,690,917, the applicant describes an invention which has as its object new aminoesters of the formula:

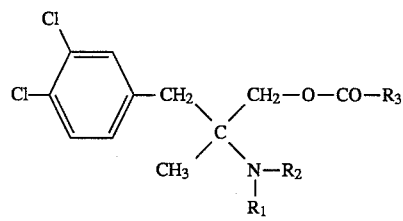

in which:

$R_1$ is H or low-molecular-weight alkyl, $R_2$ is low-molecular-weight alkyl, low-molecular-weight phenylalkyl, low-molecular-weight cycloalkylalkyl; or $R_1$ and $R_2$ together, with the nitrogen atom to which they are bound, form a five- to seven-chain saturated heterocyclic compound which can comprise a second heteroatom such as oxygen not juxtaposed with nitrogen; $R_3$ is low-molecular-weight alkyl, cycloalkyl, or low-molecular-weight phenylcycloalkyl, pyridyl, or phenyl, low-molecular-weight phenylalkyl, low-molecular-weight diphenylalkyl, optionally hydroxylated, low-molecular-weight phenylalkenyl, optionally mono-, di- or trisubstituted by chlorine atoms, low-molecular-weight alkyl radicals, low-molecular-weight alkoxy, or trifluoromethyl, acetamide or acetyloxy radicals.

These compounds exhibit analgesic properties associated with action on the central nervous system (CNS), while having no effects on the gastrointestinal tract.

DETAILED SUMMARY OF THE INVENTION

The object of the present invention is new esters derived from 2-allylamino-2-(3,4-dichlorobenzyl)-n-propanol, their method of
preparation and their application in therapeutics, especially for their antiallergic properties.

The allylaminoesters of the invention have the formula (I):

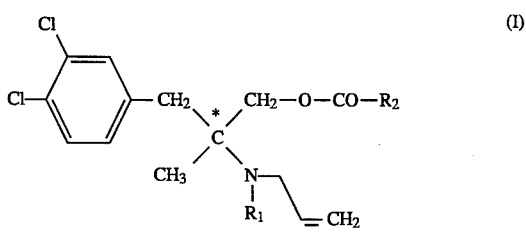

in which:

$R_1$ is H or low-molecular-weight alkyl, $R_2$ is low-molecular-weight alkyl, cycloalkyl, or low-molecular-weight phenylcycloalkyl, pyridyl, or phenyl, low-molecular-weight phenylalkyl, low-molecular-weight diphenylalkyl, low-molecular-weight phenylalkenyl, in which the phenyl cycle may be mono-, di- or trisubstituted by chlorine atoms, low-molecular-weight alkyl radicals, low-molecular-weight alkoxy, or trifluoromethyl, acetamide or acetyloxy radicals.

In all the compounds, the preferred substances are those in which $R_1$ is methyl and $R_2$ is methyl, phenyl or pyridyl, and further, the invention preferentially relates to the enantiomers of the compounds (I) with an absolute (S) configuration, established according to the Cahn-Ingold-Prelog rule. The addition salts of the esters (I) with the acids are also included in the invention.

More precisely with respect to the compounds, "low-molecular-weight radicals" are to be understood as linear or branched radicals containing 1 to 5 carbon atoms. The alkoxy radicals are more specifically methoxy radicals.

Examples of the acids, especially the therapeutically acceptable acids, used in the preparation of the addition salts are mineral or organic acids such as acetic, benzenesulfonic, camphorsulfonic, citric, ethanesulfonic, fumaric, hydrobromic, hydrochloric, lactic, maleic, malic, methanesulfonic, nitric, pamoic, phosphoric, salicylic, stearic, succinic, sulfuric and tartaric acid.

A further object of the invention is a method of preparation of the aminoesters (I) from allylaminoalcohols of the formula (II):

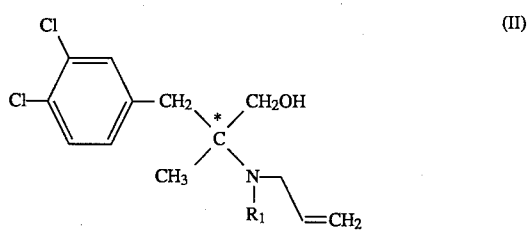

in which $R_1$ is H or low-molecular-weight alkyl, which consists in involving them in alcoholysis reactions according to the diagram:

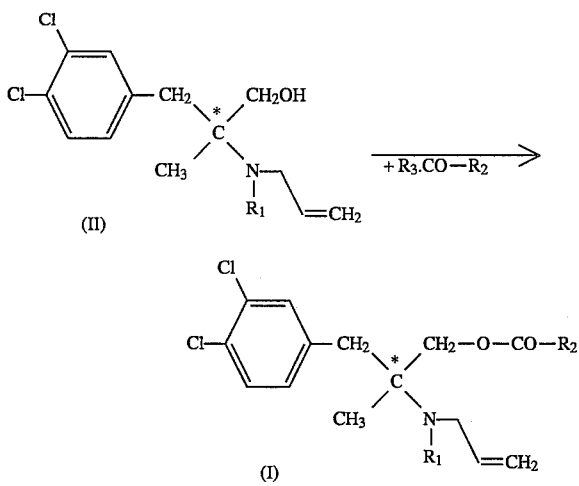

on substrates R₃—CO—R₂ (III) in which:

R₃ represents a halogen atom X which is preferably chlorine or bromine, the acyl halogenide R₂—CO—X (IV) being brought into the process according to a procedure A, R₃ represents a labile radical —OR₄, in which R₄ is low-molecular-weight alkyl containing 1 to 4 carbon atoms and is preferably methyl or ethyl, the ester of the formula R₂—CO—OR₄ (V) being brought into the process via a procedure B.

To implement the method, the racemic allylaminoalcohols (II) can be prepared as described in Examples 7 and 13 (R₁=H, R₁=CH₃) of U.S. Pat. No. 4,994,617. The corresponding (S)-configuration enantiomers being prepared according to a method adapted from that described in that same patent or according to that of U.S. Pat. No. 5,348,980. This latter preparation consists either in resolving their corresponding racemic compounds or, preferentially, in reacting (S)-(−)-2-amino-2-(3,4-dichlorobenzyl)-n-propanol, prepared according to Example 1C of U.S. Pat. No. 4,994,617, with an allyl halogenide in an inert solvent to obtain (S) allylaminoalcohol (II) in which R₁ is hydrogen; and then performing reduction methylation with formaldehyde and formic acid according to the Eschweiler-Clarke method to obtain (S) allylaminoalcohol (II) in which R₁ is CH₃. As previously described, Procedure A, which consists in obtaining the allylaminoesters (I) by alcoholysis of acyl halogenides (IV) under the action of allylaminoalcohols (II), is performed by various techniques which are amply described in the literature (Sonntag, *Chem. Rev.* 52, 237–416 (1953), pages 312 to 324).

The halogenides (IV) used are available commercially or are prepared by reacting mineral acid halogenides such as thionyl chloride, phosphorus pentachloride or phosphorus pentabromide with the corresponding R₂—COOH acids.

The alcoholysis reaction per se consists in reacting Compounds (II) and (IV) in an anhydrous aprotic solvent such as benzene, toluene, diethyl ether, tetrahydrofurane, dioxane, acetone, acetonitrile, pyridine, dimethylformamide, methylene chloride, or chloroform, which is the preferred solvent.

An acid acceptor can optionally be added to the reaction medium. This agent can be mineral or organic. Examples are sodium or potassium carbonates, the corresponding bicarbonates, or triethylamine or pyridine.

An alternative method is first to prepare the metallic alcoholates of the allylaminoalcohols (II) in situ and then to cause them to react with Compounds (IV). The metallic alcoholates are prepared by the action of alkaline metals such as sodium, sodium hydride or sodium amide, or by reaction with sodium ethylate or potassium tertiobutylate in the presence of a compatible inert solvent. For example, the metallation reaction consists in reacting 1 mole of allylaminoalcohol (II) dissolved in 5 to 20 parts of dimethyl formamide with 0.9 to 1.1 mole of sodium hydride; the formation reaction of the alcoholate is usually complete in 1 to 3 hours at a temperature of 0° to 30° C. The N-allylaminoesters (I) are obtained by reacting one mole of (II) or its alcoholate, dissolved in 5 to 20 parts of appropriate solvent, with 0.6 to 1.8 mole of acyl halogenide (IV). However, the preferred ratios for one mole of (II) or its alcoholate are 8 to 15 parts of solvent and 0.8 to 1.3 mole of halogenide (IV). The reaction is then allowed to proceed at a temperature of between 10° and 110° C. for a period of 1 to 24 hours.

The reaction, conducted between 20° and 60° C. for 3 to 7 hours, preferentially leads to satisfactory yields of the ester (I).

The compounds (I) are isolated from the reaction medium and are purified by conventional methods such as extraction, crystallization, or column chromatography.

According to Procedure B, the alcoholysis of the above-defined esters (V) by means of the allylaminoalcohols (II) yields the substances of the invention (I) by transesterification according to the reaction:

which is performed in solution in the anhydrous aprotic solvents in the presence of acidic or basic catalysts. Removal of the R₄OH alcohol formed is advantageous, and is accomplished by adding to the medium alcohol-sequestering agents such as molecular sieves of suitable porosity or by removing the alcohol by distillation as it forms. This latter method is preferred, and leads, on the one hand, to the use of the esters (V) in which R₄ is an alkyl radical containing 1 to 3 atoms of carbon, to obtain low-boiling-point R₄OH alcohols such as methyl, ethyl, propyl or isopropyl alcohol, and on the other hand, to the use as reaction solvents of benzene, toluene or the xylenes, which combine with the aforesaid alcohols to form low-boiling-point azeotropes.

The acidic or basic catalysts can be mineral and/or organic in nature. Basic catalysts are preferred, however, such as alkaline or non-alkaline metals and derivatives thereof, such as, for example, potassium tertiobutylate, aluminum triisopropylate, magnesium methylate, sodium, sodium hydride, sodium ethylate and sodium methylate, these last alcoholates being especially preferred.

In practice, the reaction consists in dissolving one mole of allylaminoalcohol (II) in 10 to 50 parts by weight of the appropriate solvent, and then adding to the solution 1.1 to 2.0 moles of ester (V). After the addition of 0.025 to 0.05 mole of catalyst, the mixture is heated to a sufficient temperature to remove by distillation the alcohol formed or its azeotrope with the solvent. This temperature can be between 50° and 130° C. and can be maintained for 1 to 6 hours to obtain satisfactory results. One especially valued technique is to add the catalyst by fractions or continuously during the reaction, and, also in the case of azeotropic distillation, to add solvent during the reaction to make up for the losses from distillation.

The preferred conditions are to dissolve 1 mole of alcohol (II) and 1.25 to 1.75 mole of ester (V) in which R₄ is methyl in 25 to 35 parts by weight of toluene, referred to the quantity of (II) used. The solution is heated to 65°–75° C., 0.025 to 0.05 mole of sodium methylate is added, and the toluene-methanol azeotrope formed is distilled slowly for 1 to 2 hours. A further 0.0125 to 0.025 mole of sodium methylate is added and the solution is distilled for 30 minutes to 1 hour; this last operation is repeated once more. The products of the reaction are then isolated and purified by the aforesaid techniques.

EXAMPLES

The invention is illustrated non-restrictively by the following examples, which are based on the use of Procedures A and B described above.

The purity, identity and physicochemical characteristics of the substances of the invention are determined, as follows:

- The purity is checked by thin-layer chromatography on silica gel. The Rf observed in the elution solvent used is given in the examples.
- The identity of the substances obtained with the proposed structures is checked on the basis of their proton nuclear magnetic resonance spectrum at 60 to 90 MHz, the substances being dissolved in deutero chloroform with tetramethylsilane as an internal reference, and when they are examined in their salified form, by first displacing the base away from its salt in situ. The nature of the signals, their chemical shifts in ppm and the number of protons that they represent are noted.
- For the substances obtained in crystalline form, the crystallization solvent is indicated, as is the uncorrected melting point determined by the capillary tube method.

EXAMPLE 1:
(R.S)-1-acetyloxy-2-[(N-allyl)-methy(amino]-2-methyl-3-(3,4-dichlorophenyl)-n-propyl. ($R_1=R_2=CH_3$.)

Procedure A.

In a 200-ml reaction vessel protected against humidity, 6.0 g (20.8 mmol) of (R,S)-2-[(N-allyl)-methylamino]-2-(3,4-dichlorobenzyl)-n-propanol are dissolved in 75 ml of anhydrous chloroform. The mixture is stirred at 20° C. for 15 minutes and 2.0 g (25.3 mmol) of acetyl chloride are added concurrently.

The solution is heated under reflux conditions for 5 h. Following vacuum distillation over a water bath, the residue is dissolved cold in 75 ml of 2N hydrochloric acid solution. The solution is extracted three successive times with 25 ml of ether.

The ethereal phases are removed; the acid phase is alkalized to a pH of 12 at 5° C. with concentrated sodium hydroxide solution (d=1.33), and then extracted three times with 25 ml of ether.

The ethereal phases are washed by extraction with saturated sodium chloride solution and are then dried over $SO_4Na_2$.

After the ether has been evaporated, the oily product is purified by column chromatography (Merck Ref. 9385 silica gel (R) 60).

Elution with a mixture of methylene chloride and acetone in a ratio of 95:5 (v:v) yields the purified product in the form of a viscous oil.

Weight=5.3 g Yield=77.1% Molar equivalent=329.5 (theoretical 330.2) TLC: Rf=0.40–0.50 (methylene chloride-acetone 9:1 v:v) 1H NMR 1.00 (s, 3H); 2.10 (s, 3H); 2.32 (s, 3H); 2.87 (d, 2H) 3.2 (d, 2H); 4.00 (s, 2H); 5.00–5.30 (m, 2H); 5.60–6.00 (m, 1H); 7.00–7.40 (m, 3H).

Hydrochloride 5.1 g (15.4 mmol) of the above product are dissolved in 60 ml of anhydrous methylene chloride. 12 ml of 4N hydrochloric ether solution are added at a temperature below 10° C. The solution is stirred for 2 h at ambient temperature, and the solvents are then evaporated under vacuum over a water bath. The residue, dissolved in 75 ml of methylene chloride, is subjected to the same treatment again with 10 ml of 4N hydrochloric ether solution.

The amorphous crude residue is purified in 80 ml of petroleum ether. The product is filtered and is dried under vacuum at 40° C.

Weight=5.0 g MP [melting point]=94° C. Yield=98%

EXAMPLE 2:
(S)-1-acetyloxy-2-[(N-allyl)-methylamino]-2-methyl3-(3,4-dichlorophenyl)-n-propyl. ($R_1=R_2=CH_3$.)

Procedure A.

The substance is prepared according to the procedure of the preceding example, from (S)-2-[(N-allyl)-methylamino]-2-(3,4-dichlorobenzyl)-n-propanol[;] $[\alpha]_D^{20}=+13°$ C. (c=1, N HCl) and acetyl chloride. The ester is obtained with a yield of 44% after chromatographic purification.

Molar equivalent=328.3 (theoretical 330.2) TLC: Rf=0.40–0.50 (methylene chloride-acetone 9:1 v:v) 1H NMR signals and shifts: same as those of the compound of Example 1.

EXAMPLE 3:
(R,S)-1-benzoyloxy-2-[(N-allyl)-methylamino]-2-methyl-3-(3,4-dichlorophenyl)-n-propyl. ($R_1=CH_3$, $R_2=C_6H_5$.)

Procedure A.

Preparation according to Example 1, from (R,S)-2-[(N-allyl)methylamino]-2-(dichloro-3,4-benzyl)-n-propanol and benzoyl chloride. Yield after purification=45%. Molar equivalent=390.5 (theoretical 392.4).

TLC: Rf=0.60–0.65 (methylene chloride-acetone 9:1 v:v) 1H NMR 1.10 (s, 3H); 2.40 (s, 3H); 2.80 (s, 2H); 3.30 (d, 2H) 4.30 (s, 2H); 5.00–5.30 (m, 2H); 5.60–6.00 (m, 1H); 7.00–8.10 (m, 8H).

Hydrochloride

Yield=86% MP=84° C. (ethanol)

EXAMPLE 4:
(R,S)-1-acetyloxy-2-allylamino-2-methyl-3-(3,4-dichlorophenyl)-n-propyl. ($R_1=H$; $R_2=CH_3$.) "Alternate"

Procedure A.

In a 250 ml reaction vessel protected against humidity and in a nitrogen atmosphere, 14.0 g (51 mmol) of (R,S)-2-allylamino-2-(3,4-dichlorobenzyl)-n-propanol are added by portions over a period of 20 minutes to 1.25 (51 mmol) of sodium hydride suspended in 45 ml of anhydrous dimethylformamide.

The reaction caused by the addition is slightly exothermic. The greenish suspension obtained is stirred for one hour at 20°–25° C., and 3.3 ml (46 mmol) of pure acetylchloride are then added at 20° C. for a period of approximately 15 minutes. A beige precipitate forms during this addition.

The mixture is stirred for one hour at ambient temperature and is then precipitated in 800 ml of ice water.

The aqueous suspension is adjusted to a pH of 1 by the addition of concentrated hydrochloric acid, and is then extracted three successive times with 125 ml ether.

The ethereal phases are removed. The acidic aqueous phase is alkalized cold to a pH of 12 by the addition of concentrated sodium hydroxide solution (d=1.33) and is then extracted three times with 100 ml ether.

The combined ethereal phases are washed by extraction with a saturated sodium chloride solution and are then dried on $SO_4Na_2$. After the ether has been evaporated, the residue, weighing 10.2 g, is purified by column chromatography (Merck Ref. 9385 silica gel 60). Elution with a mixture of methylene chloride and acetone in a ratio of 95:5 (v:v) yields the purified product in the form of a viscous oil.

Weight=4.3 g Yield=26.7% Molar equivalent=312.4 (theoretical 316.2) TLC: Rf=0.60–0.65 (methylene chloride-acetone 9:1 v:v) 1H NMR 1.00 (s, 3H); 1.50 (s, broad, 1H exchangeable with $D_2O$); 2.10 (s, 3H); 2.70 (s, 2H); 3.25 (d, 2H); 3.90 (s, 2H), 5.00–5.40 (m, 2H); 5.70–6.20 (m, 1H); 6.90–7.40 (m, 3H).

Hydrochloride
Yield=78% MP=165° C. (ethyl acetate)

EXAMPLE 5:
(R,S)-1-benzoyloxy-2-allylamino-2-methyl-3-(3,4-dichlorophenyl)-n-propyl. ($R_1$=H, $R_2$=$C_6H_5$.)

Procedure B.

In a reaction vessel protected against humidity are placed successively 280 ml of anhydrous toluene, 9.0 g (32.8 mmol) of 2-allylamino- 2-(3,4-dichlorobenzyl)-n-propanol and 6.7 g (49.2 mmol) of methyl benzoate.

The mixture is stirred and, once the reagents are dissolved, is raised to a temperature of 65°–70° C. 1.6 ml of a 4.1M solution of sodium methylate in methanol are added drop by drop. The reaction medium is gradually heated for one hour to ensure slow distillation. The mixture is cooled to about 60° C., 0.54 ml of sodium methylate solution is added and the distillation operation is started over again.

A third and last addition of 0.54 ml of methylate solution is performed after 30 minutes of slow distillation.

After cooling to 20° C., the mixture is extracted three times with 2N hydrochloric acid solution (100–75–75 ml).

The combined acidic phases are alkalized to a pH of 12 at 10° C. by the addition of concentrated sodium hydroxide solution (d=1.33), and are then extracted three times with 75 ml of ether. The combined ethereal phases are washed by extraction with a saturated sodium chloride solution and are then dried over $SO_4Na_2$. After the ether has evaporated, the crude product (86.5 g) is purified by column chromatography (Merck Ref. 9385 silica gel (R) 60). Elution with a solution of methylene chloride and acetone in a ratio of 90:10 (v:v) yields the pure substance in the form of an oil.

Weight=10.0 g Yield=80.6% Molar equivalent=382.9 (theoretical 378.31) TLC: Rf=0.35–0.45 (methylene chloride-acetone 9:1 v:v) 1H NMR 1.10 (s, 3H); 1.40 (s, 1H exchangeable $D_2O$); 2.80 (s, 2H); 3.30 (d, 2H); 4.20 (s, 2H); 5.00–5.35 (m, 2H); 5.70–6.15 (m, 1H); 6.9–8.10 (m, 8H).

Hemimaleate
9.2 g (24.6 mmol) of the ester obtained above and 2.9 g (24.6 mmol) of maleic acid in 90 ml ethanol are placed under reflux conditions for 5 minutes. The solution is let stand at ambient temperature and is then cooled for one hour to 0°–5° C. The crystalline compound is filtered and is then dried under vacuum at 50° C.

Weight=9.8 g (80.5%) MP=149° C.

EXAMPLE 6:
(R,S)-1-(3-pyridyl)carbonyloxy-2-allylamino-2-methyl-3-(3,4-dichlorophenyl)-n-propyl. ($R_1$=H, $R_2$=3-pyridyl.)

Procedure B.

The compound is prepared according to the procedure of Example 5 above, from (R,S)-2-allylamino-2-(3,4-dichlorophenyl)-n-propanol and methyl nicotinate.

Viscous oil Yield=50.5% Molar equivalent=382.9 (theoretical 379.3) TLC: Rf=0.20–0.30 (methylene chloride-acetone 75:25 v:v) 1H NMR 1.00 (s, 3H); 1.20–1.30 (m, 1H exchangeable $D_2O$); 2.65 (s,2H); 3.30 (d, 2H); 4.15 (s, 2H); 5.00–5.30 (m, 2H); 5.70–6.20 (m, 1H); 6.90–7.60 (m, 3H); 8.15–8.35 (m, 1H); 8.75–8.90 (m, 1H); 9.20–9.30 (m, 1H).

Dihydrochloride
Yield=82.8% MP=121° C. (ethanol/ether)

The compounds of Examples 7 to 20 below are prepared by condensation, according to Method A, between (S)-2-[(N-allyl)methylamino]-2-(3,4-dichlorobenzyl)-n-propanol and the appropriate halogenides. The products are purified by chromatography and are obtained in the form of viscous oils. Their conformity with regard to structure and purity is checked by NMR and TLC; these results are not noted in the descriptions. The hydrochlorides of most of these substances were usually obtained in a crystalline form whose melting point is noted; some, which are indicated, were obtained in an amorphous form.

EXAMPLE 7:
(S)-1-cyclopentylcarbonyloxy-2-[(N-allyl)-methylamino]-2-methyl-3-(3,4-dichlorophenyl)-n-propyl. ($R_2$=cyclopentyl)

Base: yield=83% $[\alpha]_D^{20}$=+9.5°(c=2, ethanol)

EXAMPLE 8:
(S)-1-benzoyloxy-2-[(N-allyl)-methylamino]-2-methyl-3-(3,4-dichlorophenyl)-n-propyl. ($R_2$=$C_6H_5$)

Base: yield=67% $[\alpha]_D^{20}$=+8.5°(c=2, ethanol) Salt: hydrochloride; MP=60°–70° C.

EXAMPLE 9:
(S)-1-(4-chlorobenzoyloxy)-2-[(N-allyl)-methylamino]-2-methy3-(3,4-dichlorophenyl)-n-propyl. ($R_2$=4-Cl-$C_6H_4$)

Base: yield=60% $[\alpha]_D^{20}$=+12°(c=2.9, ethanol) Salt: hydrochloride; MP=170° C.

EXAMPLE 10:
(S)-1-(3,4-dichlorobenzoyloxy)-2-[(N-allyl)-methylamino]- 2-methyl-3-(3,4-dichlorophenyl)-n-propyl. ($R_2$=3,4-$(Cl)_2$—$C_6H_3$)

Base: yield=64% $[\alpha]_D^{20}$=+9°(c=2, ethanol) Salt: hydrochloride; MP=60°–70° C.

EXAMPLE 11:
(S)-1-(3,4-trifluoromethylbenzoyloxy)acetyloxy-2-[N-allyl)-methylamino]-2-methyl-3-(3,4-dichlorophenyl)-n-propyl. ($R_2$=3-$F_3C$—$C_6H_4$)

Base: yield=73% $[\alpha]_D^{20}$=+9°(c=2, ethanol)

EXAMPLE 12:
(S)-1(4-methyoxybenzoyloxy)-2-[(N-allyl)-methylamino]-2-methyl-3-(3,4-dichlorophenyl)-n-propyl. ($R_2$=4-$CH_3O$—$C_6H_4$)

Base: yield=52% $[\alpha]_D^{20}$=+10.5°(c=2, ethanol) Salt: hydrochloride; MP=130° C.

EXAMPLE 13:
(S)-1-(2-phenylacetyloxy)-2-[(N-allyl)-methylamino]
2-methyl-3-(3,4-dichlorophenyl)-n-propyl.
($R_1=C_6H_5$—$CH_2$)

Base: yield=74% $[\alpha]_D^{20}=+14°$(c=2, ethanol) Salt: hydrochloride; MP=125°–130° C.

EXAMPLE 14:
(S)-1-[2-(4-chlorophenyl)-acetyloxy]2-[(N-allyl)-methylamino]-2-methyl-3-(3,4-dichlorophenyl)-n-propyl.
($R_2=4$-Cl—$C_6H_4$—$CH_2$)

Base: yield=85% $[\alpha]_D^{20}=+12.5°$(c=2, ethanol)

EXAMPLE 15:
(S)-1-(2,2-diphenylacetyloxy)-2-[(N-allyl)-methylamino]-
2-methyl-3-(3,4-dichlorophenyl)-n-propyl.
($R_2=(C_6H_5)2$-CH)

Base: yield=81% $[\alpha]_D^{20}32 +26.6°$(c=2, ethanol)

EXAMPLE 16:
(S)-1-[(trans-2-phenyl-1-cyclopropane)-carbonyloxy]-2-[{N-allyl)-methylamino]-2-methyl-3-(3,4-dichlorophenyl)-n-propyl.
($R_2=C_6H_5$—CH—($CH_2$)—CH)

Base: yield=48% $[\alpha]_D^{20}=+19.8°$(c=2, ethanol)

EXAMPLE 17:
(S)-1-cinnamoyloxy-2-[(N-allyl)-methylamino]-2-methyl-3-(3,4-dichlorophenyl)-n-propyl.
($R_2=C_6H_5$—CH=CH)

Base: yield=59% $[\alpha]_D^{20}=+21°$(c=2, ethanol)

EXAMPLE 18:
(S)-1-(4-chlorocinnamoyloxy)-2-[(N-allyl)-methylamino]-2-methyl-3-(3,4-dichlorophenyl)-n-propyl.
($R_2=4$-Cl—$C_6H_4$—CH=CH)

Base: yield=38% $[\alpha]_D^{20}=+21°$(c=2, ethanol) Salt: hydrochloride - amorphous substance

EXAMPLE 19:
(S)-1-nicotinoyloxy-2-[(N-allyl)-methylamino]-2-methy-3-(3,4-dichlorophenyl)-n-propyl.
($R_2=3$-pyridyl)

Base: yield=50% $[\alpha]_D^{20}=+8°$(c=2, ethanol) Salt: hydrochloride - amorphous substance

EXAMPLE 20:
(S)-1-isonicotinoyloxy-2-[(N-allyl)-methylamino]2-methyl-3-(3,4-dichlorophenyl)-n-propyl.
($R_2=4$-pyridyl)

Base: yield=61% $[\alpha]_D^{20}=+6°$(c=2, ethanol) Salt: hydrochloride - amorphous substance Toxicity and pharmacological tests The acute toxicity of the compounds in animals has been found to be low. Pharmacological studies reveal that the compounds possess antihistaminic action at both the bronchial and the vascular levels when administered orally or intravenously, providing grounds for their use in the treatment of a variety of allergic reactions, more specifically those triggered by histamine.

The acute toxicity of the compounds has been studied by oral administration in the male mouse. For this purpose, the substances were administered in aqueous solution at a rate of 2 ml per 100 g body weight. The animals were observed for three hours after administration and then daily for 14 days, after which they were sacrificed and autopsied.

The LD50s (lethal doses causing death in 50% of the animals) were calculated according to the method of J. L. Reed and H. Muench (Am. J. Hyg. 27 (1939), p. 493) and were no lower than 1000 mg/kg for the substances of the invention.

The antihistaminic properties of the allylaminoesters (I) were demonstrated by their ability to protect against histamine-induced bronchospasm in the guinea pig, as well as their ability in the rat to inhibit the increase in capillary permeability caused at the site of intradermal injection of a histamine solution.

Inhibition of histamine-induced bronchospasm

This study was conducted in the guinea pig by means of the bronchoconstriction test performed by the method of H. Konzett and R. Rossler (*Arch. Exp. Path. Pharmak.—Naunym Schmiedeberg* 195 (1940), 71–74), the substances of the invention being studied following intravenous administration.

The animals used in the test—male guinea pigs weighing 350 to 400 g—were prepared by the intraperitoneal (i.p.) injection of a sterile, isotonic 25% (w:v) ethyl carbamate solution in a dosage of 6.0 ml/kg, and were then fitted with a tracheal cannula for measurement of pulmonary pressure, a cannula in the right jugular vein for intravenous (i.v.) administration of the solution, and a cannula in the left carotid artery for qualitative observation of blood pressure.

The animals were then connected to a pump (Harvard, Ref. 50–1718) in order to maintain artificial ventilation at a rate of 60 insufflations per minute; the intratracheal pressure was recorded by a system comprising a transducer, an amplifier and a recorder (Gould, respective references: Ploez, 13-4615-50 and 8188-G4400-06).

Once fitted with this apparatus, the animals were allowed to rest for 10 minutes before the experiment per se was begun.

The treatment of the animals consisted in administering a series of doses of an isotonic solution of histamine hydrochloride in a dosage of 100 μmol/kg, before and after treatment with an isotonic solution of the substance under test, performed according to the following chronology:

t=−20 min—histamine (100 μmol/kg)

t=−10 min—same, control t=0 —injection of the substance under test t=+10 min—histamine (100 μmol/kg)

t=+20 min—same t=+30 min—same t=+40 min—same t=+50 min—same t=+60 min—same

The results of the tests are shown in Table 1, the activity of the substances being expressed as the percentage variation in the amplitude of bronchoconstriction calculated with respect to that triggered by the administration of a "control" dose of histamine preceding the administration of the substance under test. The % variation is calculated according to the formula:

$$\% \text{ variation} = 100 - \left( \frac{Bc(tx) - Bo(tx)}{Bc(to) - Bo(to)} \times 100 \right)$$

in which:

Bc(tx) represents the amplitude, in mm, of the bronchoconstriction at time x,

Bo(tx) the amplitude in mm of the basal respiration at time x,

Bc(to) and Bo(to) the corresponding amplitudes in mm on administration of the "control" dose of histamine preceding the administration of the substance under test.

The results are expressed as a percentage variation at the time considered and for a given concentration of the substance under test. Under these conditions, a positive percentage corresponds to a potentiating effect on bronchoconstriction, and inversely, a negative percentage corresponds to the desired inhibitory effect.

Student's t-test was used for the statistical analyses of the results. A value of $p<0.05$ was considered significant.

The average area of the papules was calculated for each lot of animals. A statistical analysis was performed by means of Student's t-test, and a percentage decrease with respect to the control lot was determined for each lot. The $ED_{50}$ (effective dose of compound which decreased the size of papules by 50% with respect to that of the control lot) was then calculated. The results of these tests are given in Table 2.

TABLE 2

INHIBITION OF THE INCREASE IN CAPILLARY PERMEABILITY CAUSED BY HISTAMINE IN THE RAT

| Compound | $ED_{50}$ mg/kg - oral route |
| --- | --- |
| Example 1 | 20.2 mg/kg |
| Example 4 | 19.8 mg/kg |
| Example 5 | 28.4 mg/kg |
| Example 6 | 27.4 mg/kg |

These test results provide convincing proof of the inhibitory action of these compounds with regard to the effects triggered by histamine in the bronchoconstriction test in the

TABLE 1

INHIBITION OF HISTAMINE-INDUCED BRONCHOSPASM IN THE GUINEA PIG

| Compound | i.v. Dose μmol/kg | % variation | | | | | | |
| --- | --- | --- | --- | --- | --- | --- | --- | --- |
| | | 1 min | 11 min | 21 min | 31 min | 41 min | 51 min | 61 min |
| Ex. 1 | 4.15 | −6.6(ns) | −83.1 | −92.5 | −94.0 | −87.3 | −90.2 | −86.3 |
| Ex. 3 | 3.40 | +0.5(ns) | −93.8 | −95.0 | −91.7 | −92.7 | −85.9 | −84.6 |
| Ex. 4 | 4.33 | −15.7(ns) | −33.0(ns) | −53.6 | −59.8(ns) | −57.1 | −58.7 | −59.6 |
| Ex. 5 | 3.62 | −14.6(ns) | −50.2 | −66.4 | −67.0(ns) | −54.0(ns) | −56.6 | −56.3 |
| Ex. 6 | 3.62 | +12.5(ns) | −29.1(ns) | −59.7(ns) | −68.3(ns) | −66.9 | −65.9 | −63.8 |
| Ex. 11 | 3.47 | −5.7(ns) | −88.2 | −97.8 | −93.3 | −91.0 | −91.9 | −91.1 |
| Ex. 12 | 3.55 | −11.6(ns) | −98.1 | −95.4 | −92.2 | −94.7 | −91.1 | −91.1 |
| Ex. 13 | 3.44 | −2.4(ns) | −84.5 | −94.2 | −97.2 | −98.4 | −98.0 | −97.2 |
| Ex. 20 | 3.56 | −7.7(ns) | −83.4 | −92..5 | −92.5 | −95.5 | −94.0 | −94.8 |

(ns): result not statistically significant

Inhibition of increase in capillary permeability

This study consisted in determining the protective effect in the rat of the compounds of the invention, administered orally, on the increase in capillary permeability caused by intradermal injection of a histamine solution in the dorsal region of the animal.

The test was performed on male Sprague-Dawley rats weighing 180 to 200 grams, who were randomized on the day of the test into groups of 6 animals per cage and were then clipped over the entire dorsal region. The test consisted in administering the substance under test orally in aqueous solution in a dosage of 1 ml solution per 100 g body weight of the animal 45 min before the injection of the histamine (t=−45), and then, 30 min after the administration of this dose (t=−15), in injecting a Bleu-Evans solution intravenously in a dosage of 0.5 ml per 100 g body weight of the animal. A histamine solution (100 μg/ml) was then injected intradermally in a dosage of 0.1 ml per injection in four separate areas on the back of each animal.

The animals were sacrificed fifteen minutes after these injections, the dorsal skin was excised, and oval blue papules were observed on the inner surface of the skin. The large diameter L and the small diameter 1 of these papules were measured and the area of each papule was determined by the formula:

area (mm$^2$)=L×l×π/4 guinea pig and their inhibitory effect on the increase in capillary permeability in the rat.

In addition, because of their activity, the compounds of the invention, in the form of appropriate pharmaceutical compositions, are also useful in human or veterinary therapy directed at the treatment of asthmatic states, especially the inhibition of states of bronchoconstriction or bronchospasm in allergic asthma or states resulting from acute or chronic bronchitis. The antihistaminic activity of the compounds also warrants their use in the treatment of symptoms triggered by the release of histamine, such as, for example, in allergies of the nasal and conjunctival mucosa, allergic rhinitis, and certain forms of edema, dermatosis, pruritus or eczema.

Due to their low toxicity, these substances can be administered in daily dosages as high as 1000 mg orally in order to obtain the anticipated effects. The usual dosage, however, is 50 to 500 mg per day orally, divided into multiple doses if necessary.

The substances of the invention or their pharmaceutically acceptable salts are administered in the form of appropriate compositions compatible with the routes adapted to the nature of the organism and to the severity of the condition to be treated.

These compositions are, for example, tablets, lozenges, capsules, powders, suppositories, gels or suspensions, or injectable, drinkable or sprayable solutions.

They are prepared by methods familiar to those skilled in the art and comprise 1 to 50% by weight of active ingredient consisting of one or several compounds of formula (I) or their salts and 99 to 50% by weight of an appropriate pharmaceutical vehicle compatible with the active ingredients and the physical form of the composition concerned.

The methods of preparation of tablets and of injectable isotonic solutes with the compounds of the invention are presented as non-restrictive examples.

Tablets

- Formula

| | |
|---|---|
| Active substance according to Example 1 | 5 to 75 mg |
| Polyvinylpyrrolidone | 2 mg |
| Carboxymethyl starch | 8 mg |
| Magnesium stearate | 3 mg |
| Lactose | 60 to 76 mg |
| Monocrystalline cellulose | 122 to 76 mg |
| for a 200 mg tablet. | |

Fabrication

Dissolve the polyvinylpyrrolidone, in a ratio of 0.1 to 1.0% by weight, in water, a low-molecular-weight alcohol such as ethanol, or a mixture of water and alcohol.

In a separate operation, intimately mix the active substance, the lactose, and half the quantity of cellulose and carboxymethyl starch and moisten this mixture with the solution previously obtained.

Granulate the paste and dry the granules so that they can be calibrated with a sieve. Add the rest of the components, mix intimately, and compress in doses of 200 mg per unit.

Isotonic solute

- Formula

| | |
|---|---|
| Active substance of Example 1 | 10 mg |
| Sodium chloride | 9 mg |
| Distilled water, sufficient quantity for | 1.0 ml |

The solute is distributed among ampuls which can be sterilized after sealing by the usual thermal methods. However, the solute is preferably sterilized by filtration and distributed in ampuls which are then sealed, these operations being performed in a sterile atmosphere.

We claim:

1. Allylaminoesters of the formula (I):

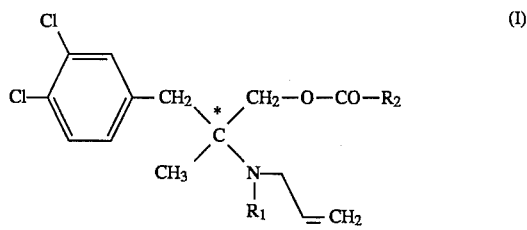

in which: $R_1$ is H or low-molecular-weight alkyl, $R_2$ is low-molecular-weight alkyl, cycloalkyl, or low-molecular-weight phenylcycloalkyl, pyridyl, or phenyl, low-molecular-weight phenylalkyl, low-molecular-weight diphenylalkyl, low-molecular-weight phenylalkenyl, in which the phenyl cycle may be mono-, di- or trisubstituted by chlorine atoms, low-molecular-weight alkyl radicals, low-molecular-weight alkoxy, or trifluoromethyl, acetamide or acetyloxy radicals, and their addition salts.

2. Allylaminoesters according to claim 1, characterized in that $R_2$ is methyl.

3. Allylaminoesters according to claim 1, characterized in that $R_2$ is methyl, phenyl or pyridyl.

4. Allylaminoesters according to claim 1, characterized in that their absolute configuration is established in the (S) form according to the Cahn-Ingold-Prelog rule.

5. An antiallergic drug characterized in that it comprises as its active ingredient an allylaminoester (I) according to claim 1 and a pharmaceutically acceptable carrier.

* * * * *